United States Patent
Koritzinsky

(10) Patent No.: US 6,494,831 B1
(45) Date of Patent: Dec. 17, 2002

(54) MEDICAL DIAGNOSTIC SYSTEM SERVICE CONNECTIVITY METHOD AND APPARATUS

(75) Inventor: Ianne Mae Howards Koritzinsky, Glendale, WI (US)

(73) Assignee: GE Medical Technology Services, Inc., Pewaukee, WI (US)

( * ) Notice: Subject to any disclaimer, the term of this patent is extended or adjusted under 35 U.S.C. 154(b) by 0 days.

(21) Appl. No.: 09/390,016

(22) Filed: Sep. 3, 1999

(51) Int. Cl.[7] .............................. A61B 5/00; H04B 17/00
(52) U.S. Cl. ........................ 600/301; 607/60; 128/904; 128/903; 340/3.51
(58) Field of Search ............................. 128/903, 904; 600/300, 301; 607/30, 32, 27, 60; 340/3.43, 3.51

(56) References Cited

U.S. PATENT DOCUMENTS

| | | | | |
|---|---|---|---|---|
| 4,361,730 A | * | 11/1982 | Barber et al. ................... | 179/5 |
| 4,860,001 A | * | 8/1989 | Tamanaka et al. ........... | 340/825 |
| 5,077,782 A | | 12/1991 | Bushue et al. ................. | 379/5 |
| 5,553,609 A | * | 9/1996 | Chen et al. .................. | 128/630 |
| 5,715,823 A | * | 2/1998 | Wood et al. ............ | 128/660.01 |
| 5,796,953 A | | 8/1998 | Zey ....................... | 395/200.57 |
| 5,818,904 A | | 10/1998 | Dean ........................... | 379/22 |
| 5,921,938 A | * | 7/1999 | Aoyama et al. ............. | 600/509 |
| 5,943,391 A | | 8/1999 | Nordling ........................ | 379/1 |
| 5,971,921 A | * | 10/1999 | Timbel ........................ | 600/300 |
| 6,074,345 A | * | 6/2000 | van Oostrom et al. ...... | 600/300 |
| 6,110,108 A | * | 8/2000 | Shimura et al. ............. | 600/300 |
| 6,137,527 A | * | 10/2000 | Abdel-Malek et al. ........ | 348/77 |
| 6,213,942 B1 | * | 4/2001 | Flach et al. .................. | 600/300 |

FOREIGN PATENT DOCUMENTS

DE  37 23 115 C  3/1989

OTHER PUBLICATIONS

Soehlke K. et al: *Interfacing A Radiology Information System And A Picture Archiving And Communication System*; IEEE Pacific Rim Conference On Communications, Computers and Signal, May 9–10, 1991, pp. 729–732, vol. 2.

* cited by examiner

Primary Examiner—Kennedy Schaetzle
(74) Attorney, Agent, or Firm—Fletcher, Yoder & Van Someren

(57) ABSTRACT

A technique is provided for verifying network connectivity between a medical diagnostic system and a remote service facility. The remote service facility is contactable at will by the subscribing system to request service, information, technical assistance, and so forth, while the service facility may also contact the subscribing system for acquisition of data, transmission of service messages, protocols, and so forth. In the connectivity verification sequence, a subscribing system is selected by the service facility and a network connection is established. A message is transmitted to the system provoking software at the system to re-establish the network connection from the system side. Two-way connectivity is thereby verified. Mobile systems may be configured to contact the service facility at their own initiation, and exchange data for permitting the service facility to re-contact the mobile system. Failure modes may be identified at various locations in the connectivity network by identification of steps in the connectivity verification process where the process failed. Alerts or other action items may be generated as a result of detected connectivity problems.

38 Claims, 5 Drawing Sheets

MEDICAL DIAGNOSTIC SYSTEM SERVICE CONNECTIVITY METHOD AND APPARATUS

FIELD OF THE INVENTION

The present invention relates generally to systems and techniques for providing remote service to medical diagnostic equipment and facilities. More particularly, the invention relates to a technique for verifying continued connectivity between a remote service facility and a subscribing medical diagnostic facility or system.

BACKGROUND OF THE INVENTION

In recent years, considerable advances have been made in medical diagnostic equipment and systems, particularly imaging systems. Such imaging systems encompass a range of modalities, each characterized by the physics involved in acquiring and processing image data. At present, medical diagnostic imaging modalities include magnetic resonance imaging (MRI) systems, x-ray systems, both digital and conventional film-based, computed tomography (CT) systems, ultrasound systems, positron emission tomography (PET) systems, and so forth. Medical facilities, hospitals and clinics make use of a wide range of such equipment, including more than one of the modalities, and in certain cases, more than one system within each modality. In larger facilities, these systems may be networked in a radiology department to permit common management or control. Such systems are increasingly associated with picture archiving and communications systems (PACS) for storing digitized image data for subsequent retrieval and reconstruction of useful images. Moreover, teleradiology applications are on the rise, in which such digitized data may be transmitted to remote locations, such as for review and diagnosis by specialized physicians and radiologists.

Regardless of the particular modality, medical diagnostic systems are often a key element in the diagnosis and treatment of disease and ailments. While certain facilities may offer their services during specific periods during the day, others require continued access to the diagnostic equipment in very demanding schedules. In both cases, the facility has a critical interest in maintaining the diagnostic equipment in good operational condition. However, due to the complexity of the systems, personnel required to review and evaluate potential problems as they arise are not often present at the location where the systems are found. Consequently, remote servicing of medical diagnostic equipment has become an important tool in maintaining the systems.

Traditionally, remote servicing of medical diagnostic equipment was performed via telephone. Operations personnel would call a remote service facility to report malfunctions and to ask questions regarding the proper operation and settings for the equipment. Where such queries could not be sufficiently handled by telephone, a service engineer was dispatched to troubleshoot the system or to provide the needed assistance.

Improvements in computer networks have greatly facilitated the task of offering assistance to medical diagnostic equipment and facilities. In particular, rather than simply calling a remote service facility and either talking directly to a technician or engineer, or awaiting a return call from a service center, network technologies have facilitated proactive techniques wherein the service center may contact the medical diagnostic equipment or facility to check the status of subscribing equipment.

Further advancements have been proposed to providing remote service to medical diagnostic systems in an effort to provide the level of service on a continual and interactive basis needed by many facilities. In one system, a remote service facility can interactively receive messages via a network, and can respond automatically to the messages either in a single connection session or in a subsequent session. Data required to analyze the state of operation of the medical diagnostic equipment can be transferred during the initial or subsequent sessions. The technique greatly facilitates identification of system problems, allows questions to be posed to the subscribing service provider, facilitates transfer of updates and imaging protocols, and permits standard and customized reports to be transmitted to subscribing systems. The interactive aspect of the technique allows the medical diagnostic facility to remain current on services provided by the remote service facility and to communicate at will with the service facility.

While these advancements in the provision of remote services to medical diagnostic equipment have greatly enhanced the level of service and information exchange, they may be subject to difficulties, particularly those arising from unanticipated connectivity problems. In particular, exchange of service information and requests on an interactive basis assumes that the remote service facility can contact the subscribing systems at will, and, conversely, that the subscribing systems can freely contact the remote service provider. Where systems operate well and no service is needed, extended periods may transpire without a contact of the service facility. If the required connection between the diagnostic equipment and the service facility is inoperative, however, service requests may not be reliably submitted to the service facility, and information from the service facility to the diagnostic system may not arrive properly or in a timely manner. Operator intervention may sometimes detect such problems, but typically only after a needed response has not been received for some time. Such delays would advantageously be avoided to insure that service problems and questions can be addressed in a timely manner.

There is a need, therefore, for a technique adapted to monitor proper connectivity of medical diagnostic equipment and facilities with a remote service provider. There is, at present, a particular need for a system which can verify two-way connectivity in which a service facility can freely contact a subscribing diagnostic system, and a diagnostic system can contact the service facility.

SUMMARY OF THE INVENTION

The present invention provides a connectivity verification technique designed to respond to these needs. The technique may be employed with any of a variety of diagnostic equipment, including specific systems of various modalities and centralized management systems, such as those typically found in large radiology departments. Where the diagnostic system is connectable to a remote service facility, the technique permits the service facility to verify that the connection can be established, both originating from the service facility and from the diagnostic equipment. Such connections may be made with specific systems, with management systems networked to the diagnostic systems at a specific facility, or both. Moreover, the connectivity verification may be timed or scheduled for automatic implementation, or could be performed manually. The system may be designed to provide at least some degree of diagnostic capabilities in which the type or location of connectivity problem is detected and recorded. Results of connectivity verifications can be stored and used to evaluate the operability of the overall system, and to improve the system where needed. Upon failure of the connectivity test, or when inconsistent or unreliable connectivity is identified, the system may permit notification via an operator, or via automated schemes, including electronic messaging, paging, and so forth. The system may be adapted both for stationary diagnostic systems, as well as for mobile systems. In the case of mobile systems, the system may be adapted to await contact of the service facility by the mobile equipment.

The technique is particularly well suited to interactive service systems in which a diagnostic facility may contact a remote service provider and a remote service provider may contact the diagnostic facility. In addition, the system is especially adaptable to service arrangements in which subscriptions or licenses are established between the service facility and the diagnostic equipment. Based upon such subscriptions, the service facility insures the connectivity between the diagnostic equipment and the service provider to allow the service provider to be contacted by the equipment managers, or automatically by the system without operator intervention.

DETAILED DESCRIPTION OF THE INVENTION

Figure 1:
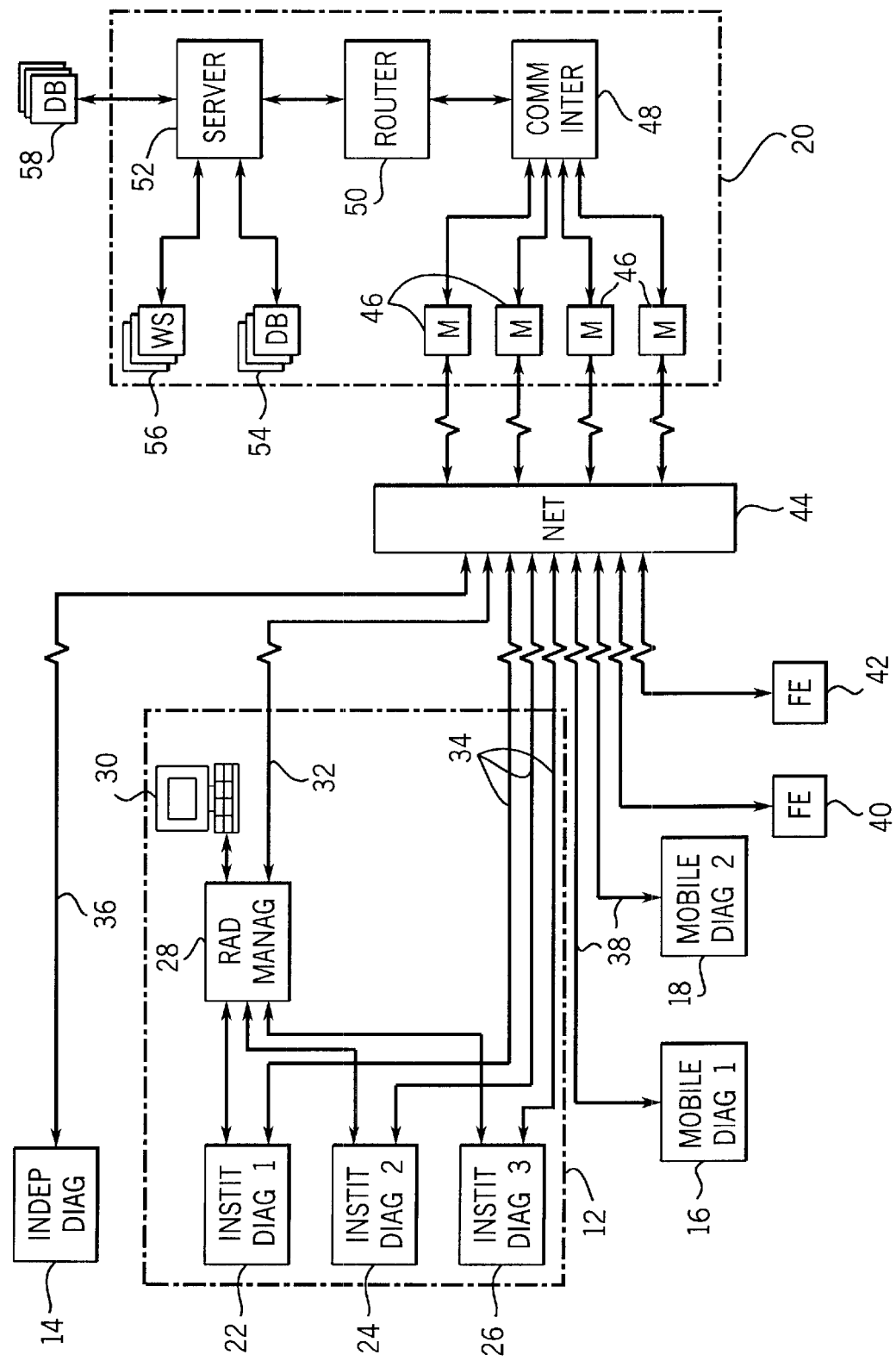
FIG. 1 is a diagrammatical representation of a series of medical diagnostic systems and facilities linked to a remote service facility over a network.

Referring now to FIG. 1, a medical diagnostic and service arrangement, designated generally by the reference numeral 10, is illustrated as including a plurality of medical diagnostic systems or stations, and a remote service facility connected by a network link. In the diagrammatic representation of FIG. 1, arrangement 10 includes diagnostic equipment provided in a central facility or institution 12, along with independent diagnostic systems 14, and mobile diagnostic systems 16 and 18. The various systems, including those within facility 12, are configured to be selectively linked to a remote service facility 20. Service facility is contacted by the systems, and may contact the systems, as required, to provide service to the systems and facilities, to address concerns or service requests transmitted from the various systems and equipment, access data from the systems, transmit data to the systems, and so forth.

In general, arrangement 10 may include any of a variety of medical diagnostic systems of various modalities. In the presently contemplated embodiment, for example, the remote service facility 20 may provide service to magnetic resonance imaging (MRI) systems, computed tomography (CT) systems, positron emission tomography (PET) systems, ultrasound systems, x-ray systems, and so forth. Moreover, the remote service facility may provide similar services to centralized medical diagnostic management systems, picture archiving and communications systems (PACS), teleradiology systems, and so forth. Such systems will typically be either stationary (i.e., located in a known place and available by a known network address) or mobile (i.e., movable and susceptible to positioning at various configurable network addresses).

As illustrated in FIG. 1, certain of the diagnostic equipment may be situated in a single facility or institution as shown diagramatically for institution 12. In the illustrated embodiment, three such diagnostic systems 22, 24 and 26 are provided in the institution. In a typical application, these systems may be similar in modality or configuration, or may be of different modalities and configurations. In a radiology department or clinic, for example, each of the imaging systems may be of a different type to provide various options to the diagnosing physicians and radiologists for imaging various anatomies and subjects of interest. Where appropriate, the systems may be networked within the facility, such as through a centralized radiology management system 28. Radiology management system 28 may permit the facility to monitor activities, performance, configurations, and other data from the diagnostic systems. Radiology management system 28 will include one or more operator work stations 30 for interfacing with the management data and software. As will be appreciated by those skilled in the art, similar operator interfaces will typically be provided for each diagnostic system 22, 24 and 26, permitting a radiologist or clinician to request and configure various examinations, to review examination results, process acquired and stored data files, and so forth. Radiology management system 28 is further provided with communications components permitting it to send and receive data over a communications link as indicated generally at reference numeral 32. Similar communications links may be provided for each of the diagnostic systems within the facility, as indicated at reference numeral 34. As described in greater detail below, these links permit data to be transferred to and from the systems over an open or dedicated network.

Various independent diagnostic systems 14 may be provided in the arrangement 10. In particular, independent clinics and departments within hospitals and institutions may possess one or more such independent diagnostic systems which may be coupled directly to the remote service facility via a communications link 36. Similarly, mobile diagnostic systems 16 and 18 may be linked directly to the remote service facility via links 38. In general, such mobile diagnostic systems may include equipment of various modalities, such as MRI or x-ray systems which may be displaced to locations to better service patient populations. Finally, arrangement 10 may include a series of field engineer stations 40 and 42 which may be similarly linked to the remote service facility to permit field service engineers to exchange data, images, schedules, reports, and the like, with the remote service facility. Such field engineers may be dispatched, for example, to respond to particular needs of subscribing systems as these arise.

Each of the systems and stations illustrated in FIG. 1 may be linked selectively to the remote service facility via a network as represented generally at reference numeral 44. For the purposes of the present technique, any acceptable network may be employed, including open and dedicated networks, virtual private networks, the Internet, and so forth. Moreover, the communications links to the network may be of any acceptable type, including conventional telephone links, cable modem links, digital subscriber lines and the like. Each of the systems is provided with communications interface hardware and software of generally known design, permitting them to establish network links with the remote service facility, and to exchange data with the facility. In the presently preferred configuration, the systems are provided with interactive software by which messages, image data, service requests, system status information, protocols, and so forth may be transmitted to and from the system by establishment of the network connection. Where desired, during periods when no such data is exchanged between the remote service facility and the subscribing system, the network connection may be terminated.

Remote service facility 20, in the diagrammatical view of FIG. 1, includes both communications components as well as components for managing provision of service to the medical diagnostic systems. Thus, a series of modems 46 are provided for establishing the network connection needed for the remote service, and for exchanging data over network 44. The modems are coupled to communications interface components as designated generally at reference numeral 48. As will be appreciated by those skilled in the art, these components and modems may include hardware and software for screening communications between the remote service facility and the medical diagnostic systems, including fire walls. Also, the modems and communications interface components may be replaced, where appropriate, with alternative communications hardware and software, such as cable modems. Communications interface components 48 are coupled to a router 50 for appropriately directing communications to and from the medical diagnostic systems coupled to the service facility via the network.

Service facility 20 is equipped to handle a variety of service requests and functions both at the initiation of the subscribing diagnostic systems, as well as by the service facility itself. In the illustrated embodiment, a server 52 is illustrated for providing the service functionalities described herein. In practice, a variety of such servers may be interlinked for various service functions, including receiving and directing service requests, proactively accessing subscribing systems for system status data, managing subscribing system licenses, and generating reports and messages for transmission to the subscribing systems. Certain of the servers may be protected by firewalls to limit access to data Server 52 may be coupled to one or more databases 54 for storing information related to the provision of services to the various subscribing medical diagnostic systems. Databases 54 may also store information relating to performance of the systems, system configurations, system license and account data, and so forth. A series of work stations 56 may be further linked to server 52, permitting service facility engineers to access data and address service concerns. By way of example, such work stations may be used to trouble shoot potential connectivity problems identified by the procedure described below. Finally, additional databases or systems, as represented generally at reference numeral 58 in FIG. 1, may be linked to the service facility to store or archive data for the systems subscribing to service from the facility. Certain of the remote facilities may be linked in similar ways in various geographical locations, such as around a single region or country, or around the world. Databases 58 may further include statistical information gathered from a population of diagnostic systems for use in analysis and service to similar systems.

Because the systems of arrangement 10 are interactively linked to the service facility, it has been found desirable to provide a means for verifying that the systems can connect to the service facility at will and, conversely, that the service facility can readily access the subscribing medical diagnostic systems. In general, where a system experiences technical difficulties or where service requests arise, the inability to contact the service facility may result in delay in addressing the service concerns. Similarly, even where service concerns are received from the systems, where the systems cannot be recontacted by the service facility, alternative and potentially time consuming measures must be taken to provide the desired feedback. The present technique provides a mechanism for insuring connectivity between the medical diagnostic systems and the service facility.

Figure 2:
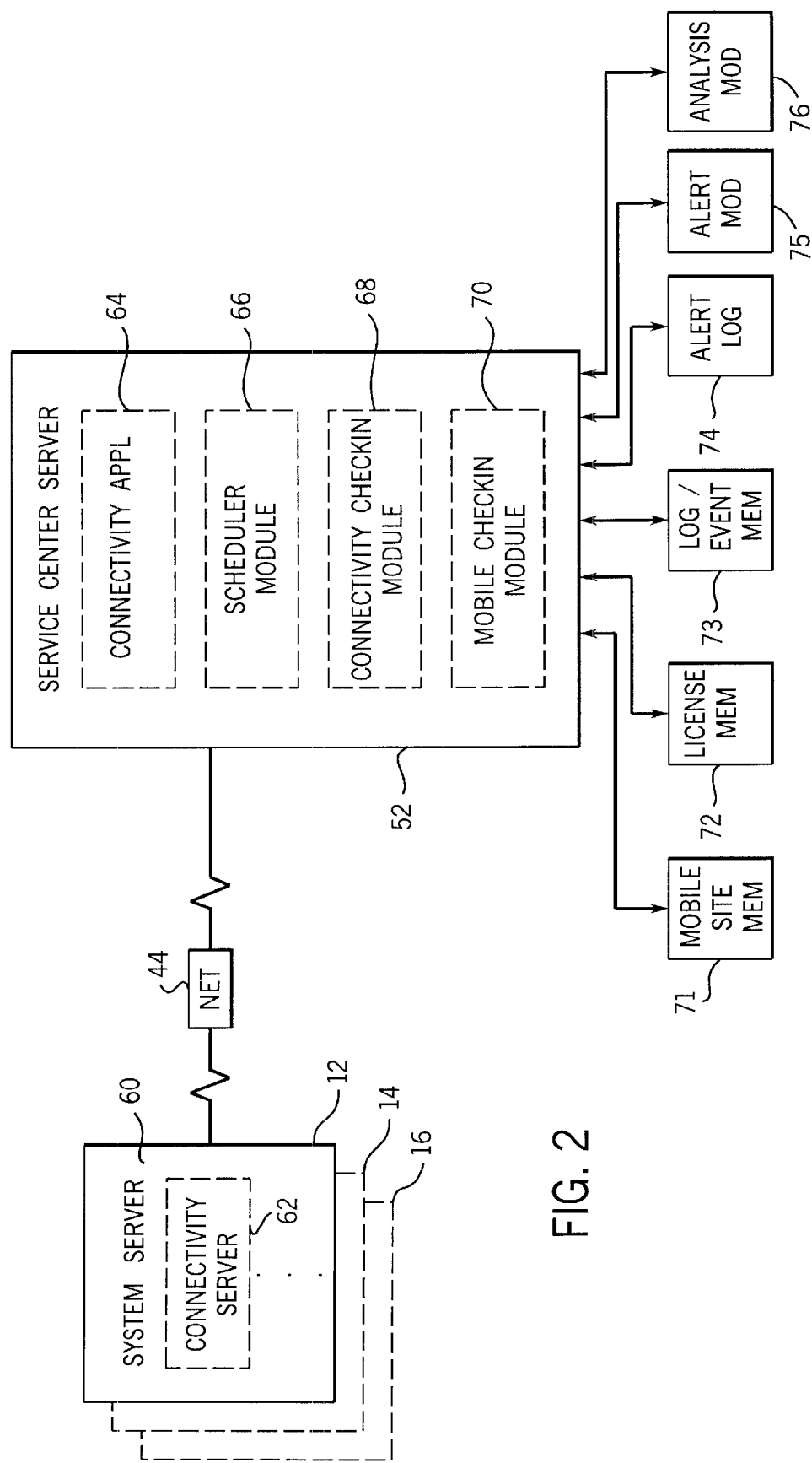
FIG. 2 is a diagrammatical representation of certain of the functional components of one of the diagnostic systems shown in FIG. 1 and of the remote service facility.

FIG. 2 illustrates, certain of the functional components of the diagnostic systems and of the service facility designed to provide verification of connectivity. The components are specifically designed to enable connections initiating from either the medical diagnostic equipment or from the remote service facility. In a presently preferred embodiment, both the subscribing equipment and the service facility include network servers and server software designed to provide for interactive exchange of data via the network link. Such servers may be based on any known or suitable software or protocol, exchanging data, for example, in accordance with Point-to-Point Protocol (PPP), employing Internet Protocol (IP) packets, HyperText Transfer Protocol (HTTP), and so forth. Moreover, the servers of the systems and of the service facility are preferably designed to process and transfer data in raw or processed form, such as image data processed into a standard DICOM format. Finally, the servers are preferably equipped to support HTTP applications, and include a browser capable of displaying interactive pages, such as in HTML, XTL, or other language configurations, and to support java applications, applets, servlets and similar code for carrying out the functions described herein.

In the diagrammatical representation of FIG. 2, the subscribing diagnostic system includes a system server 60 which calls upon a connectivity servlet 62 for verifying the status of communications components. As will be appreciated by those skilled in the art, servlet 62 may be defined by any appropriate code installed at the system or transferred to the system upon demand. As described more fully below, in fixed or stationary systems, the servlet will be called upon in response to receipt of a connectivity verification message from the remote service facility, and will thereafter recontact the service facility to verify that the two-way connections can be readily established. In mobile systems, the connectivity servlet is adapted to contact the service facility upon displacement of the mobile system to a new location, and to receive a verification response to the initiated contact.

Within the remote service facility, one or more servers 52 are equipped with a series of software modules designed to initiate and respond to connectivity verification messages. In the diagrammatical representation of FIG. 2, the server includes a connectivity application 64 which manages the connectivity functions described below. A scheduler module 66 defines timing and contacts initiated by the remote service facility for the connectivity verification sequences of subscribing medical diagnostic systems. A connectivity check-in module 68 serves to receive and exchange data with diagnostic systems during the connectivity sequences executed by application 64 in accordance with the schedules established by module 66. A similar mobile check-in module 70 manages exchange of data with mobile diagnostic systems upon initiation of connectivity verification sequences with those systems.

Server 52 and the coded modules accessed by it are further interfaced with blocks of memory for storing data used in the connectivity verification process. These blocks of memory may be defined in any acceptable medium, such as disc drives, magnetic tape, optical memory devices, solid state memory, and so forth. As illustrated in FIG. 2, memory blocks are provided for mobile sites, as indicated at reference numeral 71, storing configuration parameters for subscribing mobile sites, as well as system identifications, locations, access or address numbers and codes, and so forth. A license memory block 72 stores data indicative of the status of current service licenses for the various systems, which may include both accounting data, such information as date information, expire information, and level of service access. A log/event memory block 73 is provided to store the results of the connectivity verification sequences executed between the service center and the various subscribing systems. As indicated below, the memory block will generally include historical data indicative of the results of connectivity verification sequences. The memory block may also include references to specific events, scheduled service, service requests, and so forth. An alert log block 74 is provided for storing alerts generated by the present technique in response to a failure or anomaly in the connectivity verification sequence. Such alerts may be used to generate dispatches for service engineers both in the field and at the remote service facility to trouble shoot the communications and connection components when connectivity problems arise. An alert module 75 serves to generate alerts in response to problems with connectivity, such as electronic messages, pages, service dispatches, and the like. An analysis module 76 provides analytical capabilities, such as for recognizing patterns in connectivity problems for specific systems, or for populations of systems based upon historical records of connections and results of connectivity verification sequences.

Figure 3:
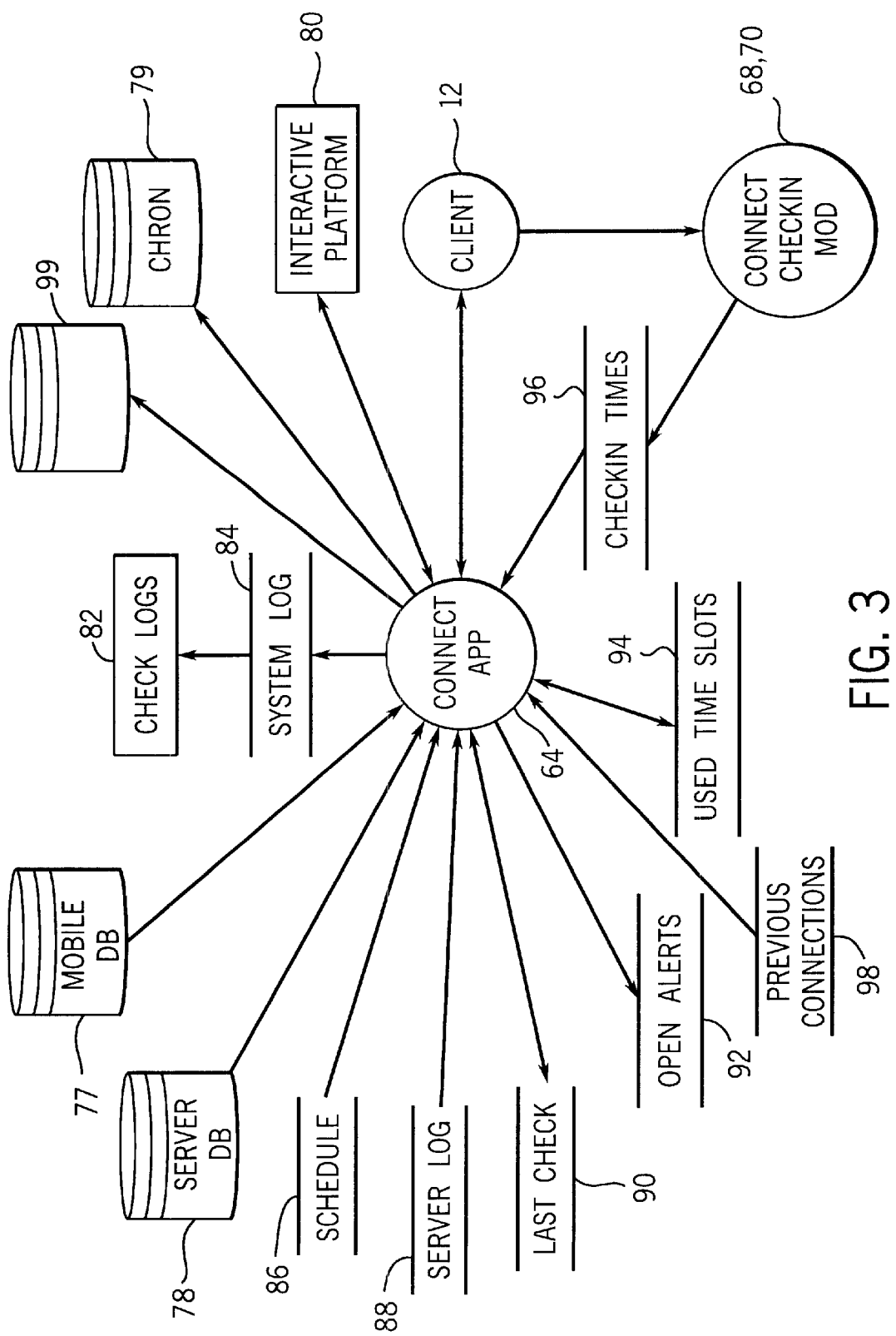
FIG. 3 is a data flow diagram illustrating certain of the signals and data exchanged between the service facility and the diagnostic equipment in a connectivity verification scheme in accordance with certain aspects of the invention.

FIG. 3 represents certain of the foregoing components and, generally, the types of data exchange between the components. As shown in FIG. 3, the connectivity application 64 provided at the remote service facility is designed to exchange data with external clients 12 in the form of medical diagnostic systems. It should be noted that the connectivity verification process is designed to insure that such data can be interactively exchanged both from the service facility to the diagnostic system, and visa-versa. The client station therefor is designed to contact and send data to connectivity check-in module 68 or 70 (depending upon the stationary or mobile nature of the client). In addition to the memory blocks represented generally at reference numerals 77, 78 and 79, which may correspond generally to memories 71, 72 and 73 described above, connectivity application 64 is designed to exchange data with an interactive software platform 80 which facilitates the exchange of service data between the remote service facility and the subscribing systems. In the presently preferred embodiment, platform 80 may provide for direct or indirect interface between actual modality components, such as MRI or CT scanners, x-ray imaging stations, and ultrasound imaging stations. The platform may also provide various service functionalities, including electronic messaging, receipt and handling of service requests and questions, image evaluation, imaging and processing protocol exchange, system configuration and data exchange, and so forth.

A log module 82 is written into by connectivity application 64 to store system log information as indicated at reference numeral 84. As noted above, such log information will typically include records of connectivity verification checks, events, service requests, and the like. Connectivity application 64 also draws upon schedule data as indicated at reference numeral 86 to identify which subscribing systems should be contacted and at what times of the day or night. As described below, because certain systems may be active or inactive at specific periods, or may be located in various time zones, the technique facilitates verification checks at various time intervals depending upon system availability and responsiveness. Server log data 88 is also accessed by connectivity application 64 for review of server activities. Data indicative of the most recent verification sequence results are stored and accessed as indicated at reference numeral 90. A log of open alerts, 92, may be accessed by connectivity application 64 as such alerts are generated, particularly as a result of failure or anomalies in the connectivity sequence as described below. A log of time slots 94 stores data indicative of the time periods during which connectivity verification sequences have been used successfully and unsuccessfully for specific subscribing systems. A log of verification or "check-in" times 96 is kept as a record of responsiveness of the subscribing systems to connectivity verification messages from the service facility, as well as mobile system-initiated verification sequences. A log of previous connections 98 may be accessed by application 64, and may serve as a basis for scheduling verification sequences, as described below. Finally, a statistical database 99 is kept with data for systems served by application 64, including connectivity statistics. It should be noted that the logical overview of FIG. 3 is provided for exemplary purposes only, and modules, memory designations, logs, and the like for specific systems may be tailored in accordance with system needs and architecture.

As described above, the present system is designed to automatically verify status of communications components for systems subscribing to remote service from the service facility. In general, automatic connectivity verification sequences may be initiated for specific subscriptions, or for all subscribing systems. Thus, where the service facility provides for interactive service arrangements with specific systems, such verification checks may be initiated and carried out on a regular or a scheduled basis. At the same time, the service facility may provide more limited offerings which do not require such connectivity verifications, or require verifications of a limited nature or on a more limited schedule.

Figure 4:
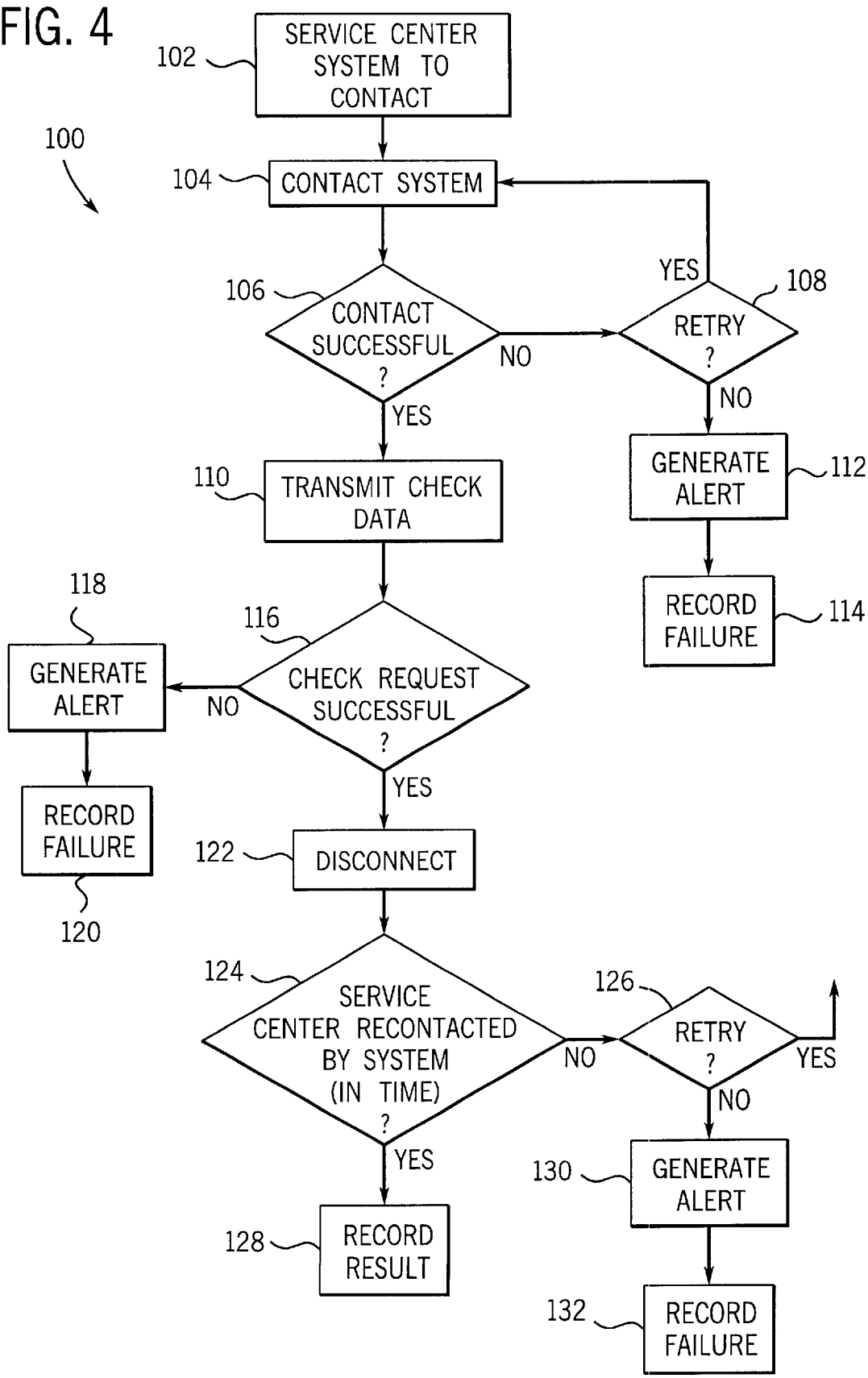
FIG. 4 is a flow chart illustrating steps in exemplary control logic for performing a connectivity verification scheme; and, FIG. 5 is a flow chart illustrating exemplary control logic for connectivity verification with a mobile diagnostic system.
Figure 5:
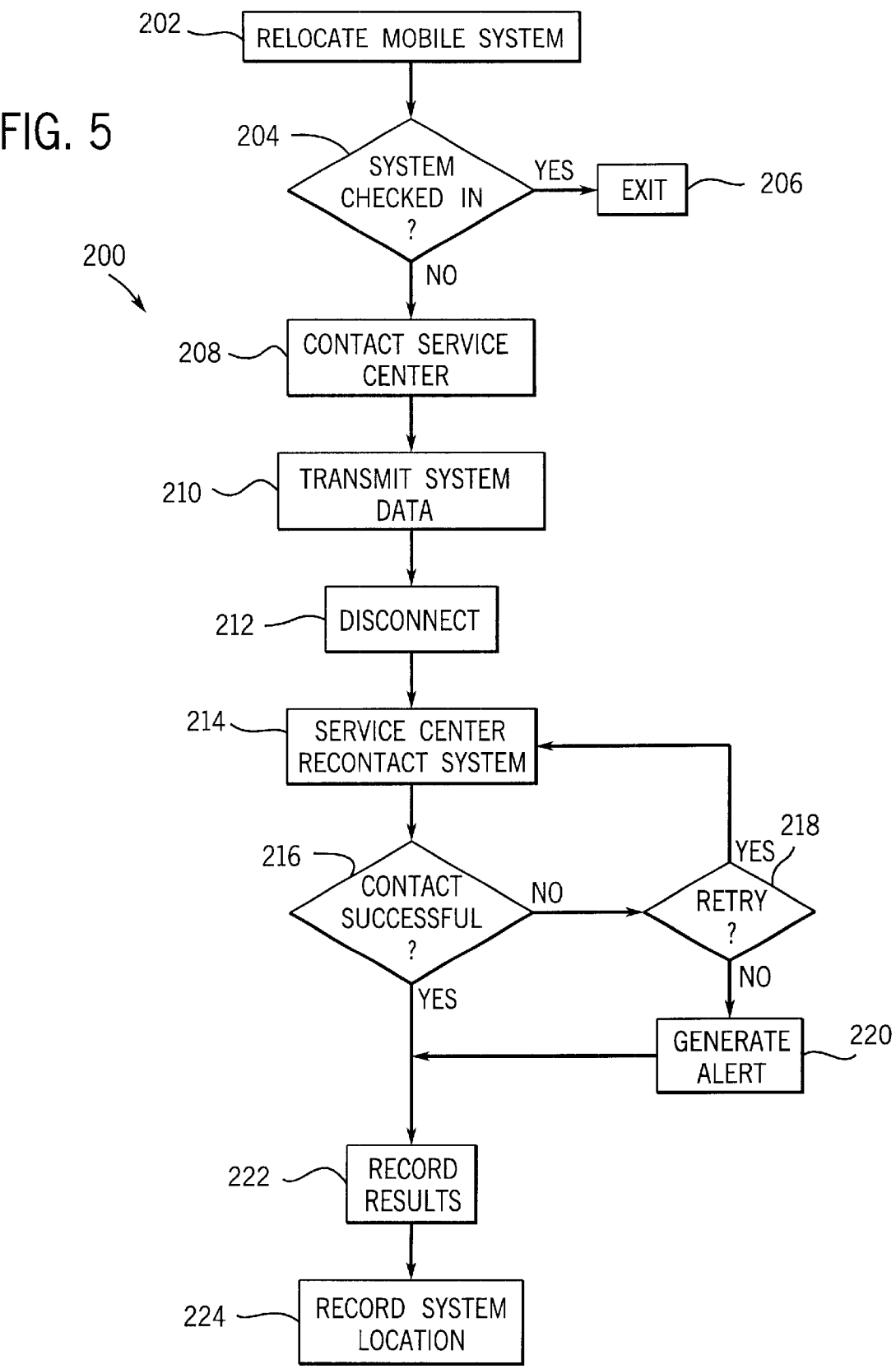

FIGS. 4 and 5 illustrate exemplary steps in control logic implemented by code at the service facility for carrying out the automatic connectivity verification techniques. FIG. 4 represents exemplary steps for verification of connectivity between the service center and systems of known location, typically situated in institutions, clinics, hospitals, and so forth. The control logic of FIG. 4, represented generally by reference numeral 100, begins at step 102 wherein a system is selected for contact. In the presently contemplated embodiment, the system is selected based upon known parameters, such as system availability, time slots for the system availability, the nature of the system, license arrangements for the provision of services to the system, system identification and address, and so forth. In general, schedules for connectivity verification may be established in advance and performed automatically. Moreover, the schedule may be at least partially based upon recent historical connections between systems and a service facility, with systems having more recently contacted the service facility being moved to a lower priority. Conversely, where historical usage data indicate that a system would have been expected to contact the service facility within a specified time or at a known frequency, such systems may be moved up in priority of scheduling. Based upon such information, the system is contacted at step 104. The contact may be made over any suitable network, typically at present over a conventional telephony line via a modem.

At step 106, the connectivity application determines whether the contact has been successfully established. If the contact is not successfully established, the system may be configured to retry the network connection as indicated at step 108. Moreover, the number of attempts to establish the connection, and the time between such attempts, may be configured by the service facility. Where such subsequent attempts are available and desired, the system will attempt such recontact by cycling back to step 104. If, at step 106, the contact is successfully established, control advances to step 110.

If the contact is unsuccessful at step 106, various measures may be taken. The inability to establish contact may be due to one of a number of factors, including the status of the diagnostic system itself, the state of transmission lines, communications hardware, software, and interface components. Moreover, for certain systems, the communications components may be occupied or simply unavailable at the period of time in which the verification sequence is initiated. If the number of attempts permitted at step 108 is exhausted, an alert is generated as indicated at step 112. The alert is stored on an alert log 74 (see FIG. 2) and may be accessed by the service facility, such as to generate a dispatch for a service engineer or to prompt operator intervention in contacting the subscribing system to investigate the nature of the connectivity problem. At step 114 the failure of the connectivity sequence is recorded in a log/event memory 73 (see FIG. 2).

Once contact is successfully established at step 106, data is transmitted between the service facility and the subscribing diagnostic system, as indicated at step 110. In the presently preferred embodiment, relatively short messages are transmitted at this step, to avoid unnecessarily occupying either the service facility or the subscribing system. In general, the data will be sufficient to provoke the code at the subscribing system to call upon the connectivity servlet and to attempt to re-establish contact with the service facility after the connection is dropped.

At step 116, the connectivity application determines whether the data has been successfully transmitted to the subscribing system. If the data has not been successfully transmitted to the system, an alert is generated at step 118, signaling to service center personnel that an inquiry should be made into the nature of the problem prohibiting the transfer of the data. The alert is stored in an alert log at the service facility. In addition, the failure of the connectivity verification sequence is recorded at step 120. If, on the other hand, the data is successfully transmitted at step 116, the service facility interrupts the connection as indicated at step 122. It should be noted that the present technique may be employed for detecting and analyzing the status of connectivity over more than one connection line. Thus, where desired, the connection established at step 104 may be disconnected as indicated at step 122, or may remain connected while the medical diagnostic system recontacts the service facility via an alternative communications route.

Following the initial contact and transfer of data as summarized above, the connectivity application awaits a return message from the subscribing system contacted. As noted above, the connectivity servlet on the subscribing system is configured to return the call initiated by the service facility to verify that two-way connectivity is functional. Thus, as indicated at step 124 in FIG. 4, the service center awaits the return call during a configurable window of time. If the wait period times out prior to receiving the call back from the subscribing system, the foregoing steps in the sequence may be repeated as indicated at step 126. Again, the number of cycles through the connectivity sequence may be set in advance. Under normal circumstances, a call is received from the subscribing system and the resulting success of the connectivity verification is recorded at step 128. In the event the sequence is repeated, following the permissible number of attempts to receive the return call, an alert is generated as indicated at step 130 and the resulting failure of the connectivity verification sequence is recorded at step 132. Such alerts may take the form, for example, of electronic messages to service personnel, pages to service personnel, service dispatches, and so forth.

As noted above, certain subscribing systems may not be regularly available during certain time slots. For example, in a presently preferred configuration, the connectivity sequence is attempted in one of three time periods distributed through a 24 hour period. If the results of the sequence summarized in FIG. 4 indicate that connection cannot be achieved at a specific time slot, an alternative time slot may be scheduled for the system-specific connectivity check sequence.

While similar logic may be employed for contacting mobile systems, particularly where the location and contact address of such systems are known, in a present embodiment, alternative control logic, summarized in FIG. 5, is employed for such systems, permitting the systems to initiate contact with the service facility. As summarized in FIG. 5, the control logic, designated generally by the reference numeral 200, begins at step 202 wherein the diagnostic system is relocated or positioned at a desired location. At step 204, the connectivity servlet at the diagnostic system determines whether a system check-in has been performed within a desired amount of time, such as subsequent to the relocation. If the check-in has been performed, the logic may be exited as indicated at step 206. If no such connectivity verification has been performed, or has not been performed within a desired amount of time, or since relocation of the system, the server at the diagnostic system initiates a network connection with the service center as indicated at step 208.

Once the connection is established, system data is transmitted at step 110, identifying the subscribing system, its location, its network address or call number, and so forth. It should be noted that, although not represented in FIG. 5, intervening logical steps may be included in this routine for signaling that a contact could not be established at step 208 or that data could not be successfully transmitted at step 210. In either event, an alert and failure event may be recorded. Once data is successfully transmitted at step 210, the mobile diagnostic system interrupts the network connection at step 212.

In response to the data received from the mobile diagnostic system, the service facility recontacts the system, as indicated at step 214. The server at the mobile diagnostic system may also be configured to await a specific amount of time for the verification call back as indicated above in the logic of FIG. 4. The service facility determines, at step 216, whether the network connection could be successfully established with the mobile system. If not, the connectivity application at the service facility may be configured to reattempt the network connection as indicated at step 218. If such attempts to recontact the system are unsuccessful, or if a desired number of reattempts expires, control advances to step 220 where an alert is generated, indicating that the connectivity verification sequence identified a connectivity failure and that additional service may be required. At step 222, the results of the connectivity verification sequence are recorded. Finally, at step 224, the system location is recorded for the purposes of any further contact which may need to be established between the service center and the subscribing mobile system.

It should be noted that the foregoing logic, whether implemented for stationary or mobile systems, provides several levels of identification of connectivity problems or failures. Specifically, because connectivity failures may involve hardware or software difficulties at various locations in the network connection, data, transfer, receipt and processing components, and so forth, it has been found useful to provide as much information in identifying a connectivity failure as possible. Such indications greatly facilitate troubleshooting of the connectivity components, providing service personnel with a clear indication of which portions of the system may be functional and which may need review, even without requiring direct involvement of personnel at the location of the system. For example, in a present configuration, a variety of failure modes may be detected based upon the point in the logic where the failure took place. Such failures may occur, for example, due to the inability of the service facility to contact the subscribing system. Failures at this point may be attributed to hardware or software which is currently occupied at the service facility, hardware or software which is currently occupied at the subscribing system, failure of the subscribing system to respond to a call, failure of the PPP module at the subscribing system to respond, an incorrect IP address, and so forth. Moreover, even once the connection is established, a failure or anomaly in the data transmission may result in identifiable failure modes. Similar failures may occur from an inability of the subscribing system to recontact the service facility. Moreover, failures may occur due to an inability to access an HTTP server or the connectivity servlet. Other events may be similarly recorded, such as the failure of the subscribing system to call back or to call back within a desired time window.

It should also be noted that the foregoing technique may be employed to verify connectivity with a large number of systems in an automated manner. The connectivity verification and response sequences may be carried out at any convenient time, such as during off-peak hours. The scheduled order of performing the verification checks may also be influenced by recent activities (e.g. data exchanges) between specific systems and the service facility. For example, where a system would be scheduled for connectivity verification but recently contacted the service facility, that system may be rescheduled for a later time, freeing the schedule for systems which have not successfully contacted the service facility within a desired time frame. Similarly, based upon historical data for a system, the service facility may move the system up on a connectivity verification schedule, considering that the inactivity may be indicative of a problem in the system connectivity hardware or software. Both for individual systems, and for entire populations of systems, the results of the connectivity verification sequences may be used for analysis of system and component performance, and for system design or improvement.

The present technique has been set forth and described herein by way of example only. The invention is not intended to be limited to this or any particular embodiment, but is intended to extend to the full legally permissible scope of the appended claims. Various alternative arrangements and configurations may be envisaged by those skilled in the art which nevertheless fall within the scope of the claims. For example, the particular configuration of the diagnostic systems, or of the service facility may be adapted to accommodate specific types of hardware, software, and so forth. Similarly, the logical steps described above for establishing and verifying the interactive network connection between subscribing systems and the service facility may be subject to a wide variety of modifications, particularly in the details related to the establishment, processing, and verification of the network connections, and in evaluations of the various failure modes.

What is claimed is:

1. A method for verifying connectivity of a medical diagnostic service system, the system including at least one medical diagnostic station and a service facility remote from the diagnostic station, the method comprising the steps of:
   (a) performing a connectivity check sequence in which a network connection is attempted between the diagnostic station and the service facility and, if the connection is established, data is transmitted from service facility to the diagnostic station;
   (b) performing a connectivity response sequence in which a second network connection is attempted between the diagnostic station and the service facility in response to the connectivity check and, if the connection is established, data is transmitted from the diagnostic station to the service facility; and
   (c) recording results of steps (a) and (b).

2. The method of claim 1, wherein step (a) is performed automatically on a scheduled basis.

3. The method of claim 1, wherein the connectivity check sequence of step (a) is initiated by the service facility.

4. The method of claim 1, wherein data necessary for attempting the connection in step is stored in a database accessed by the service facility.

5. The method of claim 4, wherein the database includes connection data for a plurality of subscribing diagnostic stations.

6. The method of claim 1, wherein the diagnostic station includes medical diagnostic equipment configured to generated image data of a subject of interest.

7. The method of claim 6, wherein the diagnostic station includes a plurality of medical imaging systems of at least one modality.

8. The method of claim 1, including the further step of generating an alert message if the attempt at step (a) or (b) is unsuccessful in establishing the respective network connection.

9. The method of claim 1, including the further step of repeating either step (a) or step (b) if the attempt to establish the respective network connection is unsuccessful.

10. The method of claim 1, wherein the diagnostic station is a mobile diagnostic station.

11. The method of claim 1, wherein step (a) is repeated during at least two different time slots to determine connectivity at corresponding times.

12. A method for verifying connectivity between a plurality of medical diagnostic stations and a remote service facility, the method comprising the steps of:
   (a) scheduling connectivity checks for each of a plurality of subscribing diagnostic stations;
   (b) initiating respective network connections between the service facility and the diagnostic stations in accordance with a schedule established in step (a) and, if the respective connection is established, transferring data to the service station;

(c) initiating respective second network connections between the service facility and the diagnostic stations in response to the data transferred in step (b); and (d) recording results of steps (b) and (c).

13. The method of claim 12, wherein the connectivity checks are scheduled within one of a plurality of different time slots.

14. The method of claim 13, wherein the time slots during which each connectivity check is scheduled is based upon past successful connectivity checks.

15. The method of claim 12, wherein a plurality of connectivity check sequences are scheduled such that an anticipated time for second network connection for a first diagnostic station overlaps with an anticipated time for a second network connection with a second diagnostic station.

16. The method of claim 12, wherein the connectivity checks are scheduled based upon subscription status for each of the plurality of diagnostic stations.

17. The method of claim 12, comprising the further step of generating an alert message if respective network connection initiated at steps (b) or (c) is unsuccessful for a diagnostic station.

18. The method of claim 12, including the further step of analyzing results of steps (b) and (c) to determine a probable failure point in the network connection.

19. The method of claim 18, including the step of recording the failure point with the results of steps (a) and (b) for a respective diagnostic station.

20. A method for verifying connectivity between a medical diagnostic system service facility and a mobile diagnostic system, the method comprising the steps of:

(a) performing a connectivity check sequence from the mobile diagnostic station to the service facility during which a network connection is initiated and, if a network connection is successfully established, data is transferred to the service facility;

(b) performing a connectivity response sequence in response to the connectivity check sequence, during which a network connection is initiated by the service facility and, if the network connection is successfully established, data is transferred to the mobile diagnostic station; and (c) recording results of steps (a) and (b).

21. The method of claim 19, wherein data transferred from the mobile diagnostic system in step (a) includes data indicative of a location of the mobile diagnostic system.

22. The method of claim 19, wherein the mobile diagnostic system is configured to perform step (a) following displacement of the mobile diagnostic system from a first location to a second location.

23. The method of claim 19, including the further step of generating an alert record if a network connection cannot be established at either step (a) or (b).

24. The method of claim 19, including the further step of generating an alert record if data cannot be accurately transferred in either step (a) or (b).

25. A method for analyzing connectivity of a medical diagnostic service system, the system including at least one medical diagnostic station and a service facility remote from the diagnostic station, the method comprising the steps of:

(a) performing a connectivity check sequence in which a network connection is attempted between the diagnostic station and the service facility and, if the connection is established, data is transmitted from service facility to the diagnostic station;

(b) performing a connectivity response sequence in which a second network connection is attempted between the diagnostic station and the service facility in response to the connectivity check and, if the connection is established, data is transmitted from the diagnostic station to the service facility;

(c) recording results of steps (a) and (b); and (d) analyzing the results stored in step (c) to determine a point of possible connectivity failure between the diagnostic station and the service facility.

26. The method of claim 24, wherein the analysis performed in step (d) includes accessing historical records for the diagnostic system from a data storage location.

27. The method of claim 24, wherein the analysis performed in step (d) includes identifying a point in step (a) at which the connectivity check sequence failed.

28. The method of claim 24, wherein the analysis performed in step (d) includes identifying a point in step (b) at which the connectivity response sequence failed.

29. The method of claim 24, wherein the connectivity check sequence and the connectivity response sequence are performed on a plurality of diagnostic stations in accordance with a predetermined schedule.

30. The method of claim 28, wherein an order of priority for each diagnostic station on the schedule is at least partially based upon historical records of network connections initiated by the respective diagnostic stations with the service facility.

31. A system for providing remote service to a medical diagnostic system, the system comprising:

a medical diagnostic system configured to process medical image data;

a service facility remote from the diagnostic system and configured to provide remote service to the diagnostic system via a network link;

first connectivity verification means at the service facility, the first connectivity verification means configured to attempt to establish a network connection with the diagnostic system in accordance with a connectivity verification routine, and to transmit data to the diagnostic system if the network connection is successfully established; and second connectivity verification means at the diagnostic system, the second connectivity verification means configured to attempt to establish a network connection with the service facility in response to the data transmitted during the connectivity verification sequence.

32. The system of claim 30, wherein the medical diagnostic system includes an imaging station of a modality selected from a group including MRI systems, x-ray systems, CT systems and ultrasound systems.

33. The system of claim 30, wherein the medical diagnostic system includes a management station coupled to at least one medical diagnostic imaging system.

34. The system of claim 30, wherein the first connectivity verification means is configured to execute the connectivity verification routine automatically based upon a predetermined schedule.

35. The system of claim 30, wherein the first connectivity verification means is configured to generate and store an alert message if the connectivity verification routine determines that two-way network communication with the medical diagnostic system cannot be successfully established.

36. A system for providing remote service to a medical diagnostic system, the system comprising:

a medical diagnostic system configured to process medical image data;

a service facility remote from the diagnostic system and configured to provide remote service to the diagnostic system via a network link;

first connectivity verification means at the medical diagnostic system, the first connectivity verification means configured to attempt to establish a network connection with the service facility in accordance with a connectivity verification routine, and to transmit data to the service facility if the network connection is successfully established; and second connectivity verification means at the service facility, the second connectivity verification means configured to attempt to establish a network connection with the diagnostic system in response to the data transmitted during the connectivity verification sequence.

37. The system of claim 35, wherein the medical diagnostic system is a mobile system displaceable between desired locations remote from the service facility.

38. A The system of claim 35, wherein the first or the second connectivity verification means is configured to generate and store an alert message if a network connection cannot be successfully established or if data cannot be successfully transferred between the diagnostic system and the service facility during the connectivity verification routine.

* * * * *